United States Patent
Meyer

(12) 
(10) Patent No.: US 7,057,050 B2
(45) Date of Patent: Jun. 6, 2006

(54) IMIDAZOLINE CORROSION INHIBITORS

(75) Inventor: George Richard Meyer, Missouri City, TX (US)

(73) Assignee: Nalco Energy Services L.P., Sugar Land, TX (US)

( * ) Notice: Subject to any disclaimer, the term of this patent is extended or adjusted under 35 U.S.C. 154(b) by 338 days.

(21) Appl. No.: 10/411,748

(22) Filed: Apr. 11, 2003

(65) Prior Publication Data

US 2004/0200996 A1 Oct. 14, 2004

(51) Int. Cl.
*C07D 233/24* (2006.01)
*C23F 11/14* (2006.01)

(52) U.S. Cl. .................................. 548/300.1; 252/394

(58) Field of Classification Search ............... 548/300.1
See application file for complete search history.

(56) References Cited

U.S. PATENT DOCUMENTS

| | | |
|---|---|---|
| 2,200,815 A | 5/1940 | Ackley |
| 2,995,520 A | 8/1961 | Luvisi et al. |
| 3,555,041 A | 1/1971 | Katz |
| 4,109,094 A | 8/1978 | Trivedi et al. |
| 4,362,737 A | 12/1982 | Schäfer et al. |
| 4,804,483 A | 2/1989 | O'Lenick, Jr. et al. |
| 4,954,635 A | 9/1990 | Rosario-Jansen et al. |
| 5,300,235 A | 4/1994 | Clewlow et al. |
| 5,322,640 A | 6/1994 | Byrne et al. |
| 6,488,868 B1 | 12/2002 | Meyer |

FOREIGN PATENT DOCUMENTS

AU    B-20678/92    11/1994

OTHER PUBLICATIONS

"The Existence of Imidazoline Corrosion Inhibitors", Valone et al., CORROSION 84, No 232, Apr. 2–6, 1984, pp. 232/1–8.

"Tall Oil Fatty Acid Anhydrides as Corrosion Inhibitor Intermediates", CORROSION 95, Fischer et al., No. 493, pp. 493/1–4.

"Mechanistic Studies of the Corrosion Inhibitor Oleic Imidazoline", Edwards et al., Corrosion Science, vol. 36, No. 2, pp. 315–325, 1994.

"The Study of Inhibitors for Sour Gas Service", Suzuki et al., Corrosion Nace, pp. 384–389, Sep. 1981.

*Primary Examiner*—Kamal A. Saeed
(74) *Attorney, Agent, or Firm*—Michael B. Martin; Thomas M. Breininger

(57) ABSTRACT

This invention provides a series of novel acrylated, substituted imidazoline corrosion inhibitors of the formula:

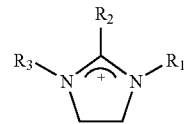

wherein $R_1$ is an alkyl radical having from 2 to 8 carbon atoms; $R_2$ is a radical derived from a fatty acid; and $R_3$ is a radical derived from an unsaturated acid and a method for inhibiting corrosion in metallic flow lines through the introduction of such inhibitors into a system wherein corrosion is sought to be precluded.

17 Claims, No Drawings

US 7,057,050 B2

IMIDAZOLINE CORROSION INHIBITORS

FIELD OF THE INVENTION

The invention relates to the preparation of novel imidazoline corrosion inhibitors and to the use of same for inhibiting corrosion in metallic flow lines.

BACKGROUND OF THE INVENTION

Flow-induced localized corrosion is a result of high shear conditions present in flow lines. The amount of corrosion that occurs is dependent on a variety of factors including the corrosiveness of the fluid flowing through the lines, the metallurgy of the line and the ability of added corrosion inhibitors to maintain adhesion to the interior of the line.

The ability of added corrosion inhibitors to maintain adhesion to the interior of the line depends on both the chemical adhesive properties of the inhibitor and the sheer stress conditions which exist inside the line. A number of products have shown promise as shear-resistant corrosion inhibitors. Included among such corrosion inhibitors are amides, quarternized amines and amide-amine salts.

While the compounds listed above have shown good adhesion characteristics, these characteristics diminish when presented with the high flow velocities present in commercial flow lines. As a result, a corrosion inhibitor with good adhesive qualities under high shear stress conditions is needed.

In U.S. Pat. Nos. 5,300,235 and 5,322,640 there has been disclosed a series of corrosion inhibitors which are acrylated tall oil fatty acid diethylenetriamine imidazolines which reflect the current understanding by those skilled in the art that to achieve satisfactory performance, such compounds must contain a hetero atom (e.g., nitrogen, oxygen or sulfur) having a nonbonding pair of electrons available for interaction with a metal surface.

While such compounds represent a significant contribution to the art of corrosion inhibition, there still remains a need for other better performing corrosion inhibitors.

It is thus an object of the present invention to provide a suitable corrosion inhibitor for inhibiting corrosion in metallic flow lines.

Another object of the present invention is to provide a process for the preclusion of corrosion in metallic flow lines.

Other aspects, objects and several advantages of the invention will be apparent from the following specification and appended claims.

SUMMARY OF THE INVENTION

This invention is based upon my discovery that the presence of a pendant group to the imidazoline ring which contains a hetero atom (nitrogen, oxygen or sulfur) having a nonbonding pair of electrons available for interaction with a metal surface is not required to achieve satisfactory corrosion inhibition. Rather, I have discovered that the acrylated imidazolines of the present invention which contain unsubstituted alkyl groups at the number 3 position and thus contain no hetero atoms and no available nonbonding electrons provide unexpectedly outstanding corrosion inhibition.

The novel imidazoline compounds of the present invention are those having the formula:

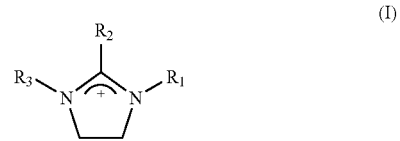

wherein $R_1$ is an alkyl radical having from 2 to 8 carbon atoms;
wherein $R_2$ is a radical derived from a fatty acid; and
wherein $R_3$ is a radical derived from an unsaturated acid.

DETAILED DESCRIPTION OF THE INVENTION

The formation of imidazolines is well known in the art. The imidazoline inhibitor of the invention may be formed as described in U.S. Pat. No. 2,874,074, issued to Johnson, the disclosure of which is herewith incorporated by reference. Further methods for the synthesis and preparation of the imidazoline inhibitor of the invention may be found in U.S. Pat. No. 2,957,000, issued to Johnson, the disclosure of which is also hereinafter incorporated by reference. The addition of substituents to the basic imidazoline structure is disclosed in U.S. Pat. No. 2,995,520 issued to Lavisi et al., the disclosure of which is hereinafter incorporated by reference.

The imidazoline inhibitor (I) of this invention may preferably be synthesized by reacting an imidazoline (II) with acrylic acid (III) as shown in the formula below:

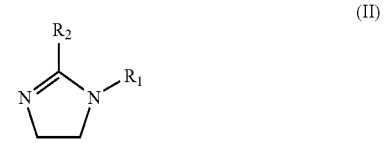

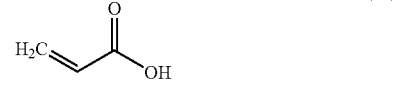

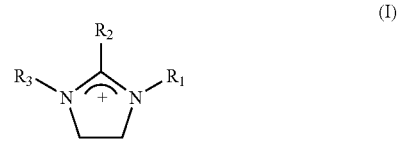

wherein $R_1$ is an alkyl radical having from 2 to 8 carbon atoms, $R_2$ is a radical derived from a fatty acid such as tall oil fatty acid (TOFA) and $R_3$ is a radical derived from the unsaturated acid.

The term TOFA as used herein is intended to define a tall oil fatty acid which is a distilled product derived from trees and which consists of a mixture of fatty acids, $C_{17} H_{31-35}$ COOH with a CAS No. 61790-12-3. It is a mixture of oleic acid as a major component, linoleic acid and saturated fatty acids. For purposes of this invention the radical obtained therefrom will be identified as heptadecenyl.

The term Acrylate as employed herein refers to the material resulting from the Michael addition of acrylic acid to the imidazoline. The addition of this chemical moiety to the structure of the molecule increases its water solubility, thus enabling it to reach metal surfaces which are submerged beneath an aqueous layer. The ability to reach such areas is critical to the successful performance of an oilfield corrosion inhibitor.

The imidazolines of this invention have been shown to be effective for inhibiting mild steel corrosion as well as corrosion of other types of metallurgy in hydrocarbon, oil/brine mixtures and aqueous systems under a variety of conditions. The inhibitor is most successful on so called sweet systems, or systems having a high $CO_2$ content. However, use of the compounds in systems with sour conditions, i.e., high $H_2S$ content, is also acceptable. Although fluid content of the flow lines may vary, the imidazoline inhibitor of the claims may be used in a variety of environments. Oil cuts in the field can range from less than 1% (oil field) to 100% (refinery) oil, while the nature of the water can range from 0 to 300,000 ppm TDS (total dissolved solids). In addition, the inhibitors of this invention would not only be useful in the large diameter flow lines, i.e., from one inch to four feet in diameter, but also would work in small gathering lines, small flow lines and headers. In the preferred method of this invention, the imidazoline inhibitor is added at any point in the flow line upflow from the point at which corrosion prevention is desired.

In a preferred embodiment, $R_2$ is derived from a fatty acid selected from the group consisting of coconut oil, beef tallow and tall oil fatty acids.

In another preferred embodiment, $R_2$ is derived from tall oil fatty acid.

In practice, the imidazoline inhibitor is preferably added to the flow line continuously to maintain a corrosion inhibiting dose of from about 0.01 to 5,000 ppm. More preferably, the corrosion inhibiting dose is from about 0.1 to about 500 ppm. In the most preferred embodiment of the invention, the corrosion inhibiting dose is from about 1 to about 250 ppm.

Although a most preferred use of the compounds of the present invention is for metallic flow lines comprising mild steel, the imidazoline inhibitors are also effective in inhibiting the corrosion in other types of metallurgy. In certain cases, batch treatments are the method of choice for application of the inhibitor. Dosage rates for batch treatment range from about 0.1 to about 50,000 ppm. In the preferred embodiment of the invention, the flow rate of the flow line in which the imidazoline inhibitor is used is between about 0 and about 65 feet per second. A more preferred flow rate is between about 0.1 to about 40 feet per second.

In some cases, the imidazoline inhibitors of the present invention may be formulated in water in order to facilitate addition to a flow line.

The present invention also provides a composition suitable for use as a corrosion inhibitor comprising an acrylated imidazoline as described above, and a carrier or diluent. The inhibitor may be present in the composition in the form of a solution or dispersion in water and/or an organic solvent. Examples of suitable solvents are alcohols such as methanol, ethanol, isopropanol, isobutanol, secondary butanol, glycols, and aliphatic and aromatic hydrocarbons.

The amount of active ingredient in the composition required to achieve sufficient corrosion protection varies with the system in which the inhibitor composition is being used. Methods for monitoring the severity of corrosion in different systems are well known and may be used to decide the effective amount of active ingredient required in a particular situation. The compounds may be used to impart the property of corrosion inhibition to a composition for use in an oil or gas field application and which may have one or more functions other than corrosion inhibition, e.g., scale inhibition.

In general it is envisaged that the inhibitors of the present invention will be used in amounts up to about 5,000 ppm, but typically within the range of about 1 to 250 ppm.

The acrylated imidazoline inhibitor compositions may be used in combination with other materials which are commonly employed in corrosion inhibiting compositions such as scale inhibitors and/or surfactants. In addition, in some instances, it may be desirable to include a biocide in the compositions.

The acrylated imidazoline corrosion inhibitors have been found to be effective corrosion inhibitors under sweet, brine and brine/hydrocarbon oil field conditions.

The following examples are intended to be illustrative of the present invention and to teach one of ordinary skill in the art to make and use the invention. These examples are not intended to limit the invention in any way.

EXAMPLE 1

Preparation of N-propyl-2-heptadecenyl Imidazoline Acrylate

Sixty grams of Tall Oil Fatty Acid (TOFA) was placed in a 250 ml, 4-neck flask equipped with an overhead stirrer, thermocouple, addition funnel and a Dean-Stark trap. The TOFA was heated to 60° C. and then 25 grams of N-propyl-ethylenediamine was added dropwise rapidly. The resulting mixture turned from light yellow to dark red and exothermed to 100° C. The mixture was then heated to 120°–140° C. for 3 hours. The hydrocarbon collected in the trap was returned to the flask. The mixture was thereafter heated to 160° C. for 1 hour while allowing water to collect in the Dean-Stark trap.

The resulting mixture was then heated at 165° C. for 2 hours and then at 225° C. for an additional hour during which time any further evolved water was collected. A nitrogen sweep was applied and the speed of the overhead stirrer was increased to facilitate removal of water. Following further heating of the mixture to 225° C. for an additional 1.5 hours, the reaction mixture was cooled and 65.9 grams of the resulting imidazoline mixture was then reacted with 18.7 grams of acrylic acid which was carefully added dropwise to the imidazoline product. A temperature rise of about 70–89° C. was observed. After exotherm had ceased, the reaction temperature was raised to about 100° C. for 2 hours. The resulting N-propyl-2-heptadecenyl imidazoline acrylate was recovered and was identified as PRODUCT 1.

EXAMPLE 2

Preparation of N-butyl-2-heptadecenyl Imidazoline Acrylate

Sixty grams of Tall Oil Fatty Acid (TOFA) was placed in a 250 ml, 4-neck flask equipped with an overhead stirrer, thermocouple, addition funnel and a Dean-Stark trap. The TOFA was heated to 60° C. and then 28.5 grams (0.245 mol) of N-butylethylenediamine was added dropwise rapidly. The resulting mixture turned from light yellow to dark red and exothermed to 84° C. The mixture was then heated to 160° C. for 3.5 hours until no further water evolved. The hydrocarbon collected in the trap was returned to the flask. The mixture was thereafter heated to 160° C. for 1 hour while allowing water to collect in the Dean-Stark trap.

Fifty grams (0.132 mole) of the resulting mixture was then heated at 225° C. for an additional hour during which time any further evolved water was collected. A nitrogen sweep was applied and the speed of the overhead stirrer was increased to facilitate removal of water. Following further heating of the mixture to 225° C. for an additional 1.5 hours, the reaction mixture was cooled and 45.25 grams of the resulting imidazoline mixture was then reacted with 10.4 grams of acrylic acid which was carefully added dropwise to the imidazoline product. A temperature rise to about 88° C. was observed. After exotherm had ceased, the reaction temperature was raised to about 120° C. for 2 hours. The resulting N-butyl-2-heptadecenyl imidazoline acrylate was recovered and was identified as PRODUCT 2.

EXAMPLE 3

Preparation of N-hexyl-2-heptadecenyl Imidazoline Acrylate

Sixty grams of Tall Oil Fatty Acid (TOFA) was placed in a 250 ml, 4-neck flask equipped with an overhead stirrer, thermocouple, addition funnel and a Dean-Stark trap. The TOFA was heated to 60° C. and 35.3 grams (0.265 mol) of N-hexylethylenediamine was added dropwise rapidly. The resulting mixture turned from light yellow to dark red and exothermed to 87° C. The mixture was heated to 160° C. for 3.5 hours until no further water evolved. The hydrocarbon collected in the trap was returned to the flask. The mixture was thereafter heated at 160° C. for 1 hour while allowing water to collect in the Dean-Stark trap.

Sixty one grams of the resulting mixture was then heated at 225°–230° C. for an hour and then at 225° C. for an additional hour during which time any further evolved water was collected. A nitrogen sweep was applied and the speed of the overhead stirrer was increased to facilitate removal of water. Following further heating of the mixture to 225° C. for an additional 1.5 hours, the reaction mixture was cooled and 55.93 grams of the resulting imidazoline mixture was then reacted in a 3-neck 250 ml flask with 18.7 grams of acrylic acid which was carefully added dropwise to the imidazoline product. A temperature rise to about 92° C. was observed. After exotherm had ceased, the reaction temperature was raised to about 120° C. for 2 hours. The resulting N-hexyl-2-heptadecenyl imidazoline acrylate was recovered and was identified as PRODUCT 3.

EXAMPLE 4

Five grams of each of the Products of Examples 1, 2 and 3 were admixed with 20 grams of isopropanol so as to form 20 percent w/w solutions of each.

Thereafter an appropriate amount of each of the resulting solutions was employed so as to provide a product concentration of each of Product 1, 2 or 3 as noted below to provide appropriate testing solutions.

The fluids were tested in accordance with the following Wheel Box Test Procedure:

The fluids utilized in the tests were 90 parts of synthetic seawater brine and 10 parts of a synthetic kerosene-like hydrocarbon which had been depolarized. The fluids were purged with carbon dioxide to saturation. The tests were run in a 7.5 ounce beverage-type bottle containing a ¼ inch×7 11/16 inch 1018 mild steel coupon with a sandblast finish. The coupon was fitted into the bottle in such a way as to remain stationary throughout the duration of the test. The initial weight of the coupon was recorded.

Two hundred ml of the test fluid (180 ml synthetic seawater and 20 ml hydrocarbon) was siphoned into the bottle with a flow of carbon dioxide to displace any air in the bottle which could mix with the corrosive fluids being poured. The desired amount of corrosion inhibitor was added to the bottle, the prepared (sandblasted and weighed) coupon was added and the bottle was capped under a blanket of carbon dioxide to displace air in the vapor phase of the bottle.

The bottle was loaded with others on a wheel testing apparatus. The wheel was preheated and set at a temperature of 176° F. The bottles were spun on the wheel at 26 rpm for 24 hours. The bottles were then removed from the wheel. The coupons were removed from the bottles and cleaned with inhibited acid, weighed and the percent protection was calculated.

The following results were obtained:

| Concentration (ppm) | Percent Protection |
|---|---|
| Product 1 (N-propyl-2-heptadecenyl) Imidazoline Acrylate | |
| 2.5 | 9 |
| 5 | 20 |
| 10 | 21 |
| 25 | 51 |
| 50 | 78 |
| 100 | 78 |
| Product 2 (N-butyl-2-heptadecenyl Imidazoline Acrylate) | |
| 10 | 63 |
| 25 | 89 |
| 50 | 89 |
| Product 3 (N-hexyl-2-heptadecenyl Imidazoline Acrylate) | |
| 10 | 78 |
| 25 | 91 |
| 50 | 91 |

EXAMPLE 5

The product of Example 1—(N-propyl-2-heptadecenyl) imidazoline acrylate was subject to a Bubble Test Procedure as follows:

A synthetic seawater brine (700 ml) was placed in a glass resin kettle where it was stirred at low speed using a magnetic stirring bar. The solution in the kettle was purged with carbon dioxide and heated to 65° C. using a hot plate with a built-in thermostat which allowed control of the temperature within 2 degrees F.

The corrosion rate was measured via the Linear Polarization Resistance technique. An electrochemical probe (Cormon) accommodating three identical carbon steel electrodes was used to obtain the polarization resistance. The electrodes were sand blasted before use. Acquisition software was utilized to convert the data obtained into corrosion rate in mils per year.

After the probe had been immersed in the brine, 300 ml of synthetic hydrocarbon was carefully introduced on top of the brine and measurement was started. The corrosion rate was plotted versus time every 15 minutes. The system was allowed to equilibrate for two hours while the baseline (base corrosion rate) was established. The carbon dioxide was switched from a purging to a blanket mode to avoid disturbing the hydrocarbon-aqueous interface. The Product 1 inhibitor was injected into the hydrocarbon phase and its effectiveness monitored continuously by the test apparatus.

The following results were obtained:

| | Percent Protection | |
|---|---|---|
| Concentration (ppm) | After 2 Hours | After 16 Hours |
| 5 | 86 | 96 |
| 10 | 97 | 99 |

The above data clearly demonstrates that the novel acrylated alkyl substituted imidazolines of the present invention

What is claimed is:

1. An imidazoline corrosion inhibitor of the formula:

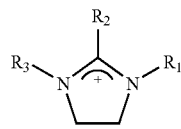

wherein $R_1$ is an alkyl radical having from 2 to 8 carbon atoms; $R_2$ is a radical derived from a fatty acid; and $R_3$ is a radical derived from an acrylic acid.

2. The imidazoline corrosion inhibitor of claim 1 wherein $R_2$ is derived from a fatty acid selected from the group consisting of coconut oil, beef tallow and tall oil fatty acids.

3. The imidazoline corrosion inhibitor of claim 2 wherein said fatty acid is a tall oil fatty acid.

4. The imidazoline corrosion inhibitor of claim 1 wherein $R_1$ is propyl.

5. The imidazoline corrosion inhibitor of claim 1 wherein $R_1$ is butyl.

6. The imidazoline corrosion inhibitor of claim 1 wherein $R_1$ is hexyl.

7. An imidazoline corrosion inhibitor selected from the group consting of
    N-propyl-2-heptadecenyl imidazoline acrylate,
    N-butyl-2-heptadecenyl imidazoline acrylate and
    N-hexyl-2-heptadecenyl imidazoline acrylate.

8. A method for inhibiting corrosion in metallic lines comprising adding to the fluid contained in the flow line a corrosion inhibiting amount of a water-soluble substituted imidazoline having the formula:

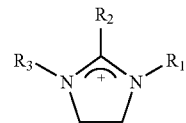

wherein $R_1$ is an alkyl radical having from 2 to 8 carbon atoms; $R_2$ is a radical derived from a fatty acid; and $R_3$ is a radical derived from an acrylic acid.

9. The method of claim 8 wherein $R_2$ is derived from a fatty acid selected from the group consisting of coconut oil, beef tallow and tall oil fatty acids.

10. The method of claim 9 wherein $R_2$ is a tall oil fatty acid.

11. The method of claim 8 wherein $R_1$ is propyl.

12. The method of claim 8 wherein $R_1$ is butyl.

13. The method of claim 8 wherein $R_1$ is hexyl.

14. The method of claim 8 wherein the imidazoline is added to the flow line continuously to maintain a corrosion inhibiting dose of from 0.01 to 5,000 parts per million.

15. The method of claim 14 wherein the flow line is comprised of mild steel.

16. The method of claim 15 wherein the flow rate of fluid through the flow line is from about 0 to about 65 feet per second.

17. The method of claim 8 wherein said imidazoline is selected from the group consisting of
    N-propyl-2-heptadecenyl imidazoline acrylate,
    N-butyl-2-heptadecenyl imidazoline acrylate and
    N-hexyl-2-heptadecenyl imidazoline acrylate.

* * * * *